(12) United States Patent
Yum

(10) Patent No.: US 8,034,605 B2
(45) Date of Patent: Oct. 11, 2011

(54) MICROBIAL MATERIALS FOR DEGRADATION OF OILS AND TOXIC CHEMICALS

(75) Inventor: Kyu-Jin Yum, Kwachon (KR)

(73) Assignee: Kyu-Jin Yum, Kwachon (KR)

( * ) Notice: Subject to any disclaimer, the term of this patent is extended or adjusted under 35 U.S.C. 154(b) by 835 days.

(21) Appl. No.: 11/826,655

(22) Filed: Jul. 17, 2007

(65) Prior Publication Data

US 2008/0032383 A1  Feb. 7, 2008

Related U.S. Application Data

(63) Continuation-in-part of application No. 10/530,653, filed as application No. PCT/KR2004/000671 on Mar. 25, 2004, now abandoned.

(30) Foreign Application Priority Data

Mar. 26, 2003  (KR) ........................ 10-2003-0018910

(51) Int. Cl.
*B09B 3/00* (2006.01)
*C12N 1/00* (2006.01)
*C12N 1/20* (2006.01)

(52) U.S. Cl. ............... 435/252.4; 435/252.5; 435/255.1; 435/256.8; 435/262.5

(58) Field of Classification Search .................. None
See application file for complete search history.

(56) References Cited

U.S. PATENT DOCUMENTS

| | | | |
|---|---|---|---|
| 3,800,977 A | 4/1974 | Stager et al. | |
| 4,803,800 A | 2/1989 | Romaine et al. | |
| 5,807,583 A | 9/1998 | Kristensen et al. | |
| 2002/0090697 A1 | 7/2002 | Hince | |

FOREIGN PATENT DOCUMENTS

| KR | 2000-0066100 A | 11/2000 |
|---|---|---|
| KR | 2002-0000444 A | 1/2002 |
| KR | 2002-084756 A | 11/2002 |

OTHER PUBLICATIONS

Romer et al., "Isolation and characterization of biarylic structure-degrading yeasts: hydroxylation potential of dibenzofuran", Environ. Pollut. vol. 118, No. 3, 2002, pp. 379-382.

*Primary Examiner* — Debbie K Ware
(74) *Attorney, Agent, or Firm* — Birch, Stewart, Kolasch & Birch, LLP.

(57) ABSTRACT

Provided is microbial materials for degradation of oils and toxic chemicals. The microbial material comprises (a) a microorganism and culture filtrate capable of degrading oil and toxic chemicals being at least one selected from the group consisting of *Trichosporon loubieri* Y1-A of deposit No. KCTC 10876BP, *Trichosporon cutaneum*, and white-rot fungi living upon the surface of wood, (b) rapeseed oils for producing more sophorolipid in surface of the said microorganism, (c) lipophilic powder being at least one selected from the group consisting of natural wax, synthetic wax, beeswax and waste candle, and (d) a microbial nutrient. This invention further comprises (e) the *Bacillus subtilis* of Deposit No. KCCM 10639 and the *Bacillus subtilis* of Deposit No. KCCM 10640. The microbial material can efficiently, rapidly degrade contaminants that are unreadily degradable, by increasing a contact area with the microorganism capable of degrading the unreadily degradable contaminants.

4 Claims, 2 Drawing Sheets

MICROBIAL MATERIALS FOR DEGRADATION OF OILS AND TOXIC CHEMICALS

CROSS-REFERENCE

This application is a continuation-in-part of U.S. application Ser. No. 10/530,853, filed Apr. 7, 2005, now abandoned. Copending U.S. application Ser. No. 10/530,653 is the U.S. National Phase of PCT application PCT/KR2004/000671 filed on Mar. 25, 2004, which claimed priority from Korean application 10-2003-018913 filed on Mar. 26, 2003. The entire contents of all are herein incorporated by reference.

TECHNICAL FIELD

The present invention relates to a microbial material for degradation of oil and toxic chemicals, and more particularly, to a microbial material which can degrade and treat oils, such as gasoline, naphtha, kerosene or Bunker C oil, and toxic chemicals, such as BTEX (benzene, toluene, ethylbenzene and xylene), which are main oil ingredients.

BACKGROUND ART

Major contaminants including, for instance, oils such as gasoline, naphtha, kerosene or Bunker C oil, toxic chemicals such as BTEX, and the like, have been leading to severe environmental contamination of nearby soil and groundwater due to poor degradability and serious toxicity.

Conventional technology for treatment of such contaminants in the soil or groundwater includes physical or chemical treatment, which, however, often has limited applicability because significant running costs are required and the soil ecosystem are severely ruined. One solution that has been proposed in recent years is biological treatment based on biodegradation by indigenous microorganisms in the contaminated soil and groundwater. However, one drawback of the use of biological treatment is that oil-to-soil cohesion or low water solubility, which results from lipophilic or hydrophobic properties of oils and toxic chemicals, makes biodegradation by the microorganisms difficult to achieve. Other problems associated with the use of biological treatment include a long process time is required and highly toxic contaminants may adversely affect activity of indigenous microorganisms, considerably lowering the overall treatment efficiency.

DISCLOSURE OF THE INVENTION

To solve the problems of the conventional biological treatment, the present invention provides microbial materials for efficiently degrading and treating environmental contaminants that are unreadily degradable, including oils, such as gasoline, naphtha, kerosene or Bunker C oil, and toxic chemicals, such as BTEX (benzene, toluene, ethylbenzene and xylene), which are main oil ingredients.

In accordance with an aspect of the present invention, there is provided a microbial material comprising (a) a microorganism and culture filtrate capable of degrading oil and toxic chemicals, (b) rapeseed oils for increasing sophorolipid quantity in surface of the said microorganism, (c) lipophilic powder and (d) microbial nutrient.

The microorganism is at least one selected from the group consisting of *Trichosporon loubieri* Y1-A of Deposit No. KCTC 10876BP, *Trichosporon cutaneum*, and white-rot fungi living upon the surface of wood. *Trichosporon loubieri* Y1-A was deposited with the Korean Collection for Type Cultures (KCTC) at the Korea Research Institute of Bioscience and Biotechnology (KRIBB), #52, Oun-dong, Yusong-ku, Taejon 305-333, Republic of Korea on Feb. 26, 2001 and assigned the International Depositary Authority Accession No. KCTC 10876BP on Dec. 2, 2005.

This invention further comprises the *Bacillus subtilis* of Deposit No. KCCM 10639 and the *Bacillus subtilis* of Deposit No. KCCM 10640, newly developed by the present inventor, as auxiliary microorganisms for degrading the oils and toxic chemicals. The *Bacillus subtilis* strains having Accession Nos. KCCM 10639 and KCCM 10640 were both deposited with the Korean Culture Center of Microorganisms (KCCM), College of Engineering, Yonsei University, 361-221, Yurim B/D, Hongie-1-clong, Seodaemun-gu, Seoul 120-091 120 749, Republic of Korea on Dec. 22, 2004.

It is well known that sophorolipid is a biosurfactant and the yeast(*Trichosporon* spp.) especially makes sophorolipid in surface of the yeast.

The present inventor thought that biosurfactant efficiently dissolves the oils and toxic chemicals from contaminated soil even without chemical surfactant, thereby improves the efficiency of degradation of oils and toxic chemicals.

The lipophilic powder is at least one selected from the group consisting of natural wax, synthetic wax, beeswax and waste candle.

The microbial nutrient includes degradable saccharide and soybean flour.

The microbial material comprises 1~5% by weight of rapeseed oils, 1~10% by weight of lipophilic powder, 0.1~1% by weight of saccharide and 0.01~0.1% by weight of soybean flour, based on the weight of the microorganism and culture filtrate used.

The microbial material according to the present invention can efficiently, rapidly degrade contaminants that are unreadily degradable, by adding highly lipophilic powder to a composition for preparing the microbial material, so that lipophilic or hydrophobic contaminants are naturally adsorbed to the surface of the powder, which increases the effective surface area for biodegradation, consequently increasing a contact area with the microorganism capable of degrading the unreadily degradable contaminants.

Since the contaminants are degraded by the microorganism in a state in which they are adsorbed to the powder surface, the amount of the toxic contaminants induced into the microorganism or adsorbed to the strain is reduced so that the toxicity against to the microorganism is weakened, thereby maintaining a stable biodegrading action.

BEST MODE FOR CARRYING OUT THE INVENTION

Figure 1:
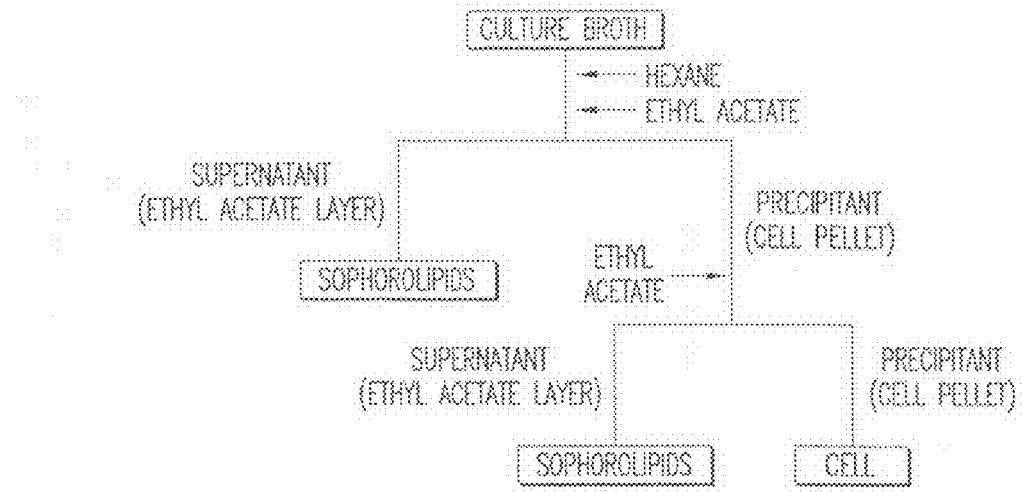
FIG. 1 is a schematic diagram for process of sophorolipid extraction.

A microbial material according to the present invention will now be described in detail.

The microbial material according to the present invention f) comprises (a) a microorganism and culture filtrate capable of degrading oil and toxic chemicals, (b) rapeseed oils for producing more sophorolipid in surface of the said microorganism, (c) lipophilic powder and (d) microbial nutrient.

The microorganism is at least one selected from the group consisting of *Trichosporon loubieri* Y1-A (Of deposit No. KCTC 10876BP), *Trichosporon cutaneum*, and white-rot fungi living upon the surface of wood.

The oils exemplified by gasoline, naphtha, kerosene, Bunker C oil and the like, and the toxic chemicals exemplified by main oil ingredients such as BTEX (benzene, toluene, ethylbenzene, xylene) or chlorophenol compounds, are unreadily degradable and highly toxic, thus causing severe environmental concerns of nearby soil and groundwater.

Useful examples of the microorganism include known microorganisms capable of degrading oils and toxic chemicals, preferably at least one selected from the group consisting of *Trichosporon* spp., *Trichosporon cutaneum* and white-rot fungi that are parasitic on the wood surface, or a mixed microorganism thereof.

More preferably, the *Trichosporon* spp. strain is *Trichosporon loubieri* Y1-A of deposit No. KCTC 10876BP newly developed by the present inventor. More preferred examples of the white-rot fungi that are parasitic on the wood surface include *Phanerocheate* spp., *Phleurotus* spp., and the like.

This invention further comprises the *Bacillus subtilis* of Deposit No. KCCM 10639 and the *Bacillus subtilis* of Deposit No. KCCM 10640, newly developed by the present inventor, as auxiliary microorganism for degrading the oils and toxic chemicals.

It is well known that sophorolipid is a biosurfactant and the yeast (*Trichosporon* spp.) especially produces sophorolipid in surface of the yeast.

The present inventor thought that biosurfactant efficiently dissolves the oils and toxic chemicals from contaminated soil even without adding of toxic chemical surfactants, thereby improves the efficiency of degradation of oils and toxic chemicals.

Accordingly the present inventor studied materials to produce more sophorolipid in surface of *Trichosphoron* spp, and found the rapeseed oil most effective to production of sophorolipid.

*Trichosphoron loubieri* Y1-A culture broth was cultivated with adding 150 ml of oleic acid, rapeseed oil, silicon oil and natural waxes, respectively, under most suitable inoculation condition as shown in Table 1.

TABLE 1

| Item | Condition |
| --- | --- |
| Volume of culture broth | 15 l |
| Medium | Potato Dextrose Broth 250 g |
| Cultivation temperature | 25 ± 2° C. |
| Cultivation time | 5 days |
| Aeration velocity | 2.5 Psi/15 l |
| Maximal yield | More than $10^8$ CFU/ml |

After cultivation of the microorganism, culture broth was set under natural condition during 48 hour to give the precipitant. Thereafter the precipitant comprising the sophorolipid was separated and obtained.

FIG. 1 is a schematic diagram for process of sophorolipid extraction.

The remaining component of oleic acid, rapeseed oil, silicon oil and natural waxes, respectively, was removed by adding 20% by volume of n-hexane based on the total volume of precipitant.

The precipitant was centrifuged after extracting the sophorolipid by ethyl acetate or ethanol.

The supernatant comprises the sophorolipid.

The amount of sophorolipid measured by centrifuge is shown in Table 2.

TABLE 2

| Additive | Oleic acid | Rapeseed oils | Silicon oils | Natural waxes |
| --- | --- | --- | --- | --- |
| Extracted sophorolipid | 18 ml/l | 34 ml/l | 7 ml/l | 22 ml/l |

According to the result shown in Table 2, the rapeseed oils produced most amount of sophorolipid in *Trichosporon loubieri* Y1-A.

The lipophilic powder is at least one selected from the group consisting of natural wax, synthetic wax, beeswax and waste candle.

As the particle size of the lipophilic powder such as wax, beeswax or used candle is reduced, the surface area per unit volume of the lipophilic powder increases, making the oils or toxic chemicals easily adsorbed to the powder binding microorganism, so that a contact area with the microorganism is greatly increased, thereby maximizing the efficiency of degrading the oil and toxic chemicals using the microorganism.

In order to enhance a survival rate of the microorganism, the microbial nutrient comprises saccharide, and preferably comprises soybean flour, which is a natural nutrient acting as an electron receptor, in place of oxygen, in an anaerobic condition.

The microbial material comprises 1~5% by weight of rapeseed oils, 1~10% by weight of lipophilic powder, 0.1~1% by weight of saccharide and 0.01~0.1% by weight of soybean flour based on the weight of the microorganism and culture filtrate.

Examples of the nutrient include various ingredients beneficial to the microorganism, such as carbon, nitrogen, vitamins or inorganic ions. Glucose or dextrose that is easily utilized by the microorganism without being subjected to biodegradation is preferably used as the source of the carbon, and soybean flour that is a naturally-occurring substance, is preferably used as the source of the nitrogen, vitamins, inorganic ions or electron receptors.

The present invention will now be described in more detail with reference to the following illustrative examples, which are given by way of illustration and are not intended to limit the scope of the present invention.

Example

*Trichosporon* spp. Strain, white-rot fungi, and *Bacillus* spp. were inoculated with 1 ml of a spore suspension in 1 l of a nutrient. The nutrient was prepared by adding 24 g of a potato dextrose broth and 10 g of lipophilic powder to 1 l of distilled water and then sterilizing all of them. The spore suspension was prepared by treating a potato agar preculture medium at a low temperature of 4° C. or less for 7 days to maximize spore forming capability to $10^7$ spores/ml or greater, and then adding 10 ml of sterile water thereto. The inoculated microorganisms were cultivated in a continuous aerated incubator to which sterile air of high pressure of 10 psi or higher is applied from a lower portion of a reactor to mix the lipophilic powders and the microorganisms, at a temperature of about 30 to about 35° C. for 3 to 5 days, giving a microorganism and culture filtrate. Then, microorganism and culture filtrate, 0.1~1% by weight of glucose and 0.01~0.1% by weight of soybean flour based on the weight of the microorganism and culture filtrate were mixed, thereby acquiring a desired product, that is, the microbial material according to the present invention.

The microbial material according to the present invention can be advantageously applied for remediation of the soil and groundwater contaminated by chlorine-based organic compounds, agricultural chemicals such as insecticides, herbicides or germicides, gasoline, kerosene, naphtha, Bunker C oil, BTEX (benzene, ethylbenzene, toluene, xylene), PAHs (polycyclic aromatic hydrocarbons) and the like.

The oil and other hydrophobic contaminant are not miscible with water in the soil and groundwater but exist in the form of an oil-based contaminant layer. Otherwise, the oil and other hydrophobic contaminant are adsorbed to organic matter in soil, such as humic acid. In the present invention, however, the oil and other hydrophobic contaminant can be adsorbed to surfaces of lipophilic, tiny-sized powder particles contained in the microbial material owing to their high lipophilic and hydrophobic properties. That is, adsorption of the oil and other hydrophobic contaminant to the powder brings about an increased surface area of the contaminants, thereby promoting degradation by selected strains efficiently capable of degrading the contaminants.

The soybean flour, which is a naturally-occurring substance added as a nutrient, acts as a source of nitrogen and vitamin for the selected strains, that is, *Trichosporon* spp. Strain, white-rot fungi, and *Bacillus* spp. Also, the soybean flour acts as a source of nitrate salts, which are final is electron receptors, in the event where oxygen in soil is exhausted during occurrence of the microbial mechanism for degradation, thereby enabling anaerobic degradation by the *Trichosporon* spp. strain, which is a facultative aerobic microbe. In such a manner, contaminants contained in a clay layer, to which it is quite difficult to feed oxygen, or in groundwater having a very low concentration of dissolved oxygen, can be effectively treated.

Experimental Example 1

1. Preparation of Contaminated Soil

Diesel oil and naphtha were mixed in the laboratory to prepare 24 l of a total petroleum hydrocarbon (TPH) solution with a concentration of 10,000 ppm to then be added to 60 l of soil intermittently sterilized at 105° C. twice for 2 hours each time, and uniformly mixed, followed by storage in a sealed container for 24 hours at room temperature, thereby finally preparing contaminated soil. Samples consisting of 4 l volumes of soil taken from the thus prepared contaminated soil were placed in 5 l flasks, and 500 ml of distilled water was then added to each flask and sealed for adjusting an appropriate water content.

2. Treatment of Contaminated Soil 21 soil samples prepared in the above-described manner were divided into seven treatment groups and 3 trials were performed on each treatment group in the following manner. The containers containing 21 samples were sealed and kept at 15° C. for 2 weeks. Thereafter, soil samples were collected from each treatment group and oils were extracted by a soil contamination testing method. Then, gas chromatography was performed using a GC-HP6890 system commercially available from Hewlett-Packard Co., U.S.A. to measure the concentration of TPH. The sealed samples were subjected to intermittent air circulation to construct the same conditions as those of field-site treatments by allowing the containers to be open to be exposed to air for about 1 minute once a day.

3. Experiment Result

The results of experiments carried out in the above-described manner are summarized in Table 3.

Treatments consist of:

① 0.1 ml of rapeseed oils+0.1 g of wax powder+0.01 g of glucose+5 ml of 100 ppm $H_2O_2$+10 ml of *Trichosporon* spp. microbial culture broth+6 ml of *Bacillus subtilis* of Deposit No. KCCM 10639 and the *Bacillus subtilis* of Deposit No. KCCM 10640 microbial culture broth ② 0.1 ml of rapeseed oils+0.1 g of wax powder+0.01 g of glucose+5 ml of 100 ppm $H_2O_2$+10 ml of *Trichosporon* spp. microbial culture broth ③ 0.1 g of wax powder+0.01 g of glucose+5 ml of 100 ppm $H_2O_2$+10 ml of *Trichosporon* spp. microbial culture broth ④ 0.1 g of wax powder+0.01 g of glucose+5 ml of 100 ppm $H_2O_2$ ⑤ 0.01 g of glucose+5 ml of 100 ppm $H_2O_2$+10 ml of *Trichosporon* spp. microbial culture broth ⑥ 0.01 g of glucose+5 ml of 100 ppm $H_2O_2$ ⑦ 5 ml of 100 ppm $H_2O_2$.

Table 3 shows TPH removal efficiency by treatment.

TABLE 3

| | Treatment | | | | | | |
|---|---|---|---|---|---|---|---|
| | ① | ② | ③ | ④ | ⑤ | ⑥ | ⑦ |
| TPH removal efficiency (%) | 97 ± 1.8 | 94 ± 2.5 | 91 ± 2.3 | 47 ± 2.3 | 69 ± 2.9 | 28 ± 2.1 | 21 ± 1.3 |

(Average ± standard deviation (3 trials))

According to the result shown in Table 3, when lipophilic wax powder and microorganisms were used in treatment (①, ②, ③), the removal efficiency was very high over about 90%, approximately 22% higher than the efficiency in the case where only the microorganism was used in treatment, which is presumably because biodegradation by the microorganism is promoted by an increased surface area for degradation of the contaminant, the increased surface area occurring when the wax powder treated together with the microorganism infiltrates into the soil and adsorbs the contaminated oil by its inherent liphophilicity.

To verify the above-described effects and principles, lipophilic powder was isolated from a soil supernatant of treatment ③ in Experimental Example 1, and only surviving cells were selectively colored green using a colorant of Acridine orange. Then, the powder surface was observed while emitting fluorescence using Confocal Laser Microscopy, and the observation result is shown in FIG. 2.

Figure 2:
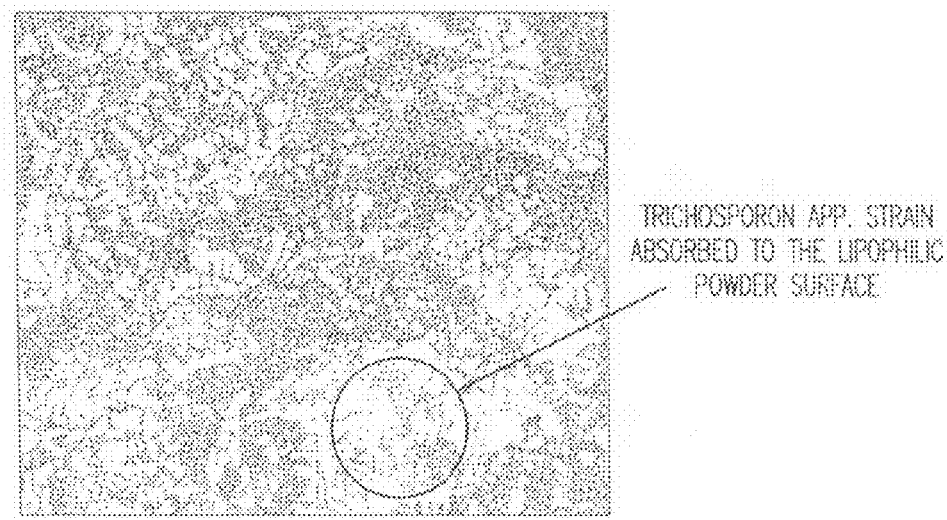
FIG. 2 is a photograph of fluorescence of activated *Trichosporon* spp. strain colored with acridine orange using a Confocal Laser Microscope with a magnification of 200 times.

As shown in FIG. 2, the overall surface of lipophilic powder was covered with surviving *Trichosporon* spp. microorganism cells used together with the powder. This suggest that contaminants adsorbed to the surface of the lipophilic powder are degraded by the *Trichosporon* spp. strain to be used as a carbon source, allowing the *Trichosporon* spp. strain cells are densely populated on the surface of the powder (dark green).

In the case that the rapeseed oils were further added to treatment ③, the removal efficiency is about 3% higher than that of treatment ③, which is presumably because amount of sopholipids produced at the surface of *Trichosporon* spp. strain dissolve the oils and toxic chemicals to smaller size.

In the case that *Bacillus subtilis* KCCM 10639 and *Bacillus subtilis* KCCM 10640 were further added to treatment ②, the removal efficiency is about 3% higher than that of treatment ②, which is presumably because both *Bacillus subtilis* degrade the oils and toxic chemicals as auxiliary microorganism for *trichosporon* spp. strain.

Experimental Example 2

Six samples of soil contaminated by crude oil were collected from six places of different depths in an actual contaminated field-site, sealed, transferred to the laboratory in a low-temperature state, and mixed well.

Treatments consist of:
① 220 g of contaminated soil+1.5 ml of sterilized *Trichosporon* spp. microbial material
② 220 g of contaminated soil+1.5 ml of *Trichosporon* spp. microbial material
③ 220 g of contaminated soil+1.5 ml of *Trichosporon* spp. microbial material cultivated after being mixed with 0.015 g of lipophilic natural wax powder.

The thus treated contaminated soils were sealed and stored at room temperature for 7 days, and the number of surviving *Trichosporon* spp. microorganisms was counted using selective media for *Trichosporon* spp. microbial strain. The result is shown in Table 4.

Figure 3:
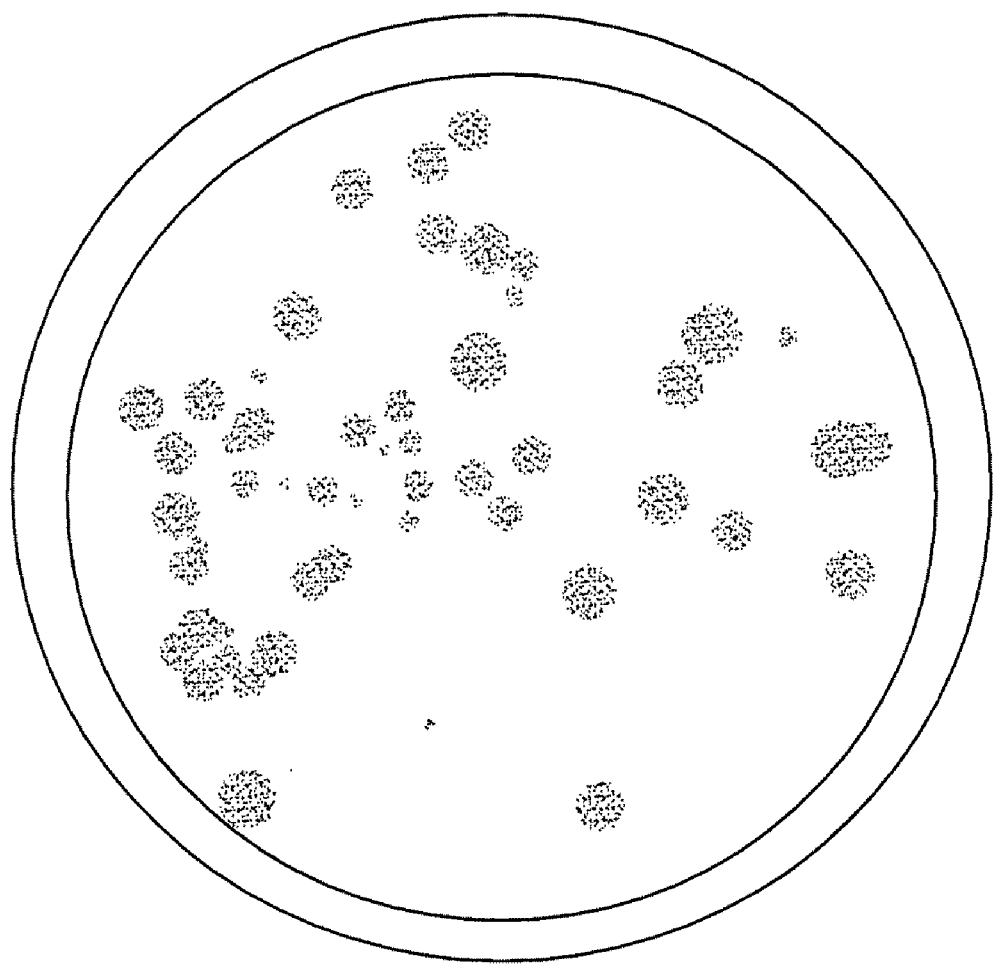
FIG. 3 shows *Trichosporon* spp. strain in the contaminated soil grown in selective media.

The selective media used were produced from PDA media added with 2 kinds of antibiotics to suppress the growth of indigenous microbes. As shown in FIG. 3, it was confirmed that only *Trichosporon* spp. strains grew.

Table 4 shows the number of surviving strains of *Trichosporon* spp. Microorganisms in 1 g of contaminated soil as expressed as colony forming units (cfu)/g.

TABLE 4

| | Treatment | | |
|---|---|---|---|
| | ① | ② | ③ |
| cfu/soil(g) | 0 | $1.7 \times 10^4$ | $1.4 \times 10^5$ |

(Values shown in Table 4 are average values of 3 trials.)

As apparent from Table 4, when a microbial material and lipophilic powder were used in treatment ③, the concentration of surviving *Trichosporon* spp. microbial strains was approximately 10 times higher than when only *Trichosporon* spp. microbial strains were used in treatment ②. Thus, it can be concluded that many *Trichosporon* spp. microorganism cells are adsorbed to the surface of the lipophilic powder to thus increase resistance to highly toxic contaminants, thereby increasing survival rate.

As described above, the microbial material according to the present invention for degradation of oils has the following advantages.

First, lipophilic ingredients contained in the microbial material increases the efficiency of degradation and the overall period for recovery of the contaminated soil and groundwater can be shortened, thereby reducing the cost for remediation of the contaminated soil and groundwater.

Second, since naturally occurring substances are used as nutrients, the cost for preparation of the microbial material can be reduced.

Third, since the naturally occurring substances containing inorganic ions and various kinds of vitamins are used, the proliferation and activity of selected microorganisms are increased, thereby increasing adaptability to the ecosystem and a survival rate.

Fourth, since the efficiency of degradation of toxic chemicals by the selected microorganism contained in the microbial material and the activity and colony forming units of the indigenous microorganisms are increased, the overall treatment efficiency is enhanced and the oil-contaminated soil and groundwater can be recovered without damaging the soil ecosystem.

Fifth, combination of the present invention treatment with the conventional treatment technologies can synergically increase the efficacy of degradation of soil and groundwater, and environmental problems associated with the conventional treatment can be solved.

Industrial Applicability

Therefore, the microbial materials for degradation of oil and toxic chemicals according to the present invention can be advantageously used in various applications of the environment industry.

What is claimed is:
1. A microbial material comprising;
   (a) at least one of *Bacillus subtilis* having Accession No. KCCM 10639 and *Bacillus subtilis* having Accession No. KCCM 10640,
   (b) a culture filtrate comprising *Trichosporon loubieri* Y1-A having Accession No. KCTC 10876BP, wherein Trichosporon loubieri Y1-A is capable of degrading at least one of gasoline, naptha, kerosene, Bunker C oil, benzene, toluene, ethylbenzene and xylene
   (c) a rapeseed oil capable of increasing production of a surfactant by *Trichosporon loubieri* Y1-A,
   (d) lipophilic powder comprising at least one of natural wax, synthetic wax, beeswax and waste candlewax, and
   (e) a microbial nutrient comprising a carbon source and/or a nitrogen source.
2. The microbial material of claim 1, wherein the microbial nutrient includes a saccharide and soybean flour.
3. The microbial material of claim 2, wherein the microbial material comprises 1 to 5% by weight of rapeseed oils, 1 to 10% by weight of lipophilic powder, 0.1 to 1% by weight of saccharide and 0.01 to 0.1% by weight of soybean flour based on the weight of the culture filtrate used.
4. A biological treatment composition for degrading environmental contaminants comprising;
   (a) at least one of *Bacillus subtilis* having Accession No. KCCM 10639 and *Bacillus subtilis* having Accession No. KCCM 10640,
   (b) *Trichosporon loubieri* Y1-A having Accession No. KCTC 10876BP capable of degrading at least one of gasoline, naptha, kerosene, Bunker C oil, benzene, toluene, ethylbenzene and xylene,
   (c) a rapeseed oil,
   (d) a lipophilic powder, and
   (e) a carbon source and/or a nitrogen source for the microorganisms.

* * * * *